(12) United States Patent  
Stockhammer et al.

(10) Patent No.: US 7,918,127 B2  
(45) Date of Patent: Apr. 5, 2011

(54) TEST METHOD FOR THE DETERMINATION OF AN OIL SEPARATION TENDENCY OF LUBRICATING GREASES AND TEST DEVICE FOR CARRYING OUT THE SAME

(75) Inventors: Raimund Stockhammer, Berlin (DE); Andreas Kömmler, Berlin (DE)

(73) Assignee: Will Vogel AG, Berlin (DE)

( * ) Notice: Subject to any disclaimer, the term of this patent is extended or adjusted under 35 U.S.C. 154(b) by 425 days.

(21) Appl. No.: 11/865,280

(22) Filed: Oct. 1, 2007

(65) Prior Publication Data

US 2008/0078238 A1   Apr. 3, 2008

(30) Foreign Application Priority Data

Oct. 2, 2006  (DE) .......................... 10 2006 047 024

(51) Int. Cl.  
    *G01N 33/26* (2006.01)
(52) U.S. Cl. ..................................... 73/53.05
(58) Field of Classification Search ............ 73/10, 53.05  
    See application file for complete search history.

(56) References Cited

U.S. PATENT DOCUMENTS

| | | | |
|---|---|---|---|
| 1,665,933 A | 4/1928 | Rodman | |
| 2,063,903 A * | 12/1936 | Bijur | 184/7.3 |
| 3,946,593 A | 3/1976 | Ruget | |
| 5,679,883 A | 10/1997 | Wedeven | |
| 7,370,514 B2 * | 5/2008 | Halalay et al. | 73/53.05 |

FOREIGN PATENT DOCUMENTS

| | | |
|---|---|---|
| DE | 20 18 265 | 12/1970 |
| DE | 94 16 284.0 | 11/1994 |

OTHER PUBLICATIONS

DE9416284—translated.*  
European Search Report (Germany Application No. 102006047024) mailed May 4, 2007.

* cited by examiner

*Primary Examiner* — Hezron Williams  
*Assistant Examiner* — Alex Devito  
(74) *Attorney, Agent, or Firm* — Fish & Richardson P.C.

(57) ABSTRACT

The invention relates to a test method and a test device for the determination of an oil separation tendency of lubricating greases under pressure load. In the method, a predetermined test pressure is applied to a test volume (2) filled with lubricating grease (27) over a predetermined test period (32), the lubricating grease (27) of the test volume (2) is contacted with an oil absorption or oil separation element (11), and the change of the test volume (2) is detected on the basis of an absorption or separation of oil (29) separated from the lubricating grease (27) by the oil absorption or oil separation element (11) at the end of the test period (32). To be able to estimate the oil separation tendency of lubricating grease more exactly, in the method according to the invention, the time history of the change of the test volume (2) representative of the oil separation is detected over the test period (32).

16 Claims, 3 Drawing Sheets

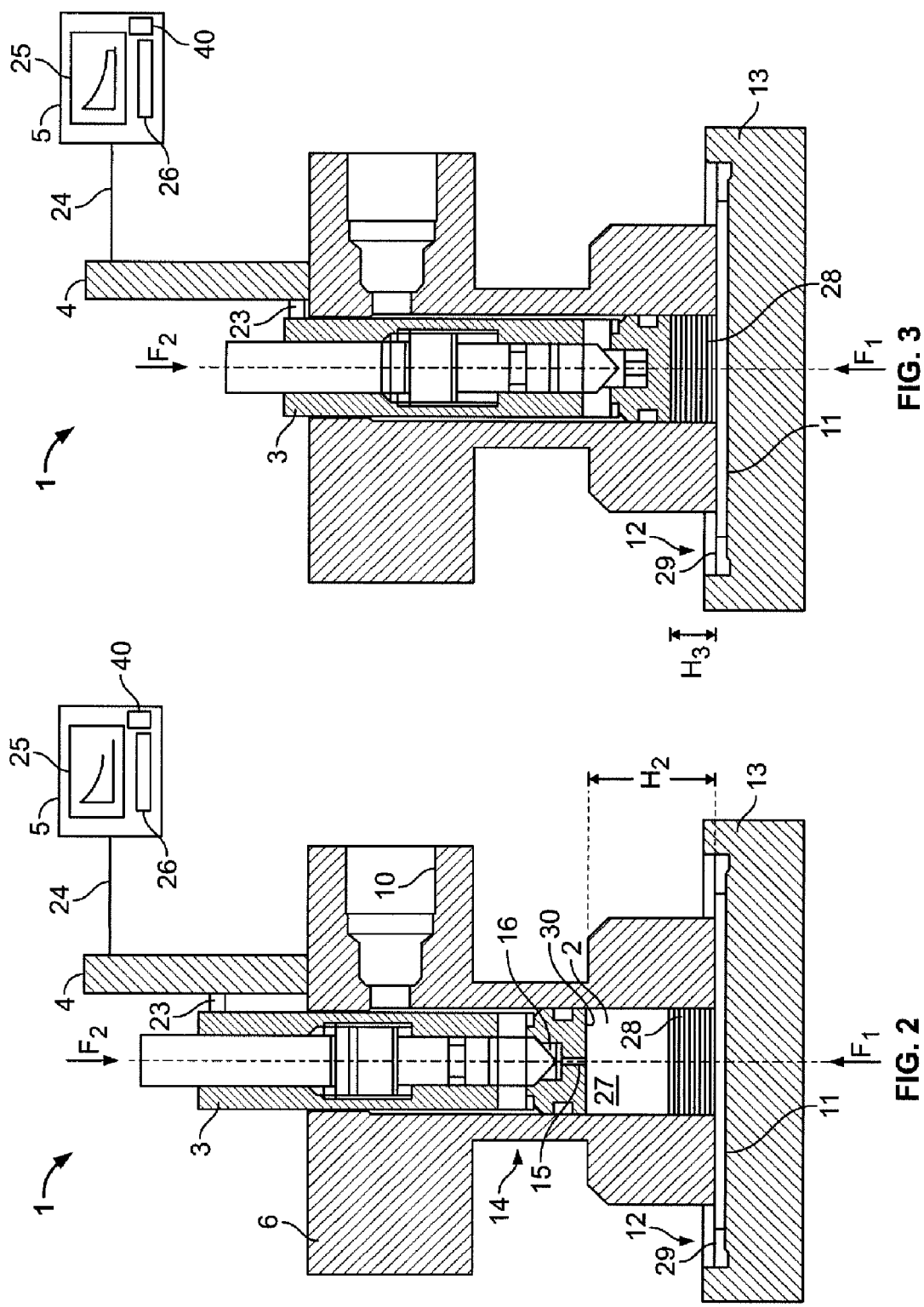

TEST METHOD FOR THE DETERMINATION OF AN OIL SEPARATION TENDENCY OF LUBRICATING GREASES AND TEST DEVICE FOR CARRYING OUT THE SAME

The invention relates to a test method for the determination of an oil separation tendency of lubricating greases under pressure load, wherein a predetermined test pressure is applied to a test volume filled with lubricating grease during a predetermined test period, the lubricating grease of the test volume is contacted with an oil absorption or oil separation element and the change of the test volume is detected on the basis of an absorption or separation of oil separated from the lubricating grease by the oil absorption or oil separation element at the end of the test period.

The invention further relates to a test device for the determination of an oil separation tendency of lubricating greases under pressure load with a test volume for receiving a lubricating grease sample, with a pressure piston limiting the test volume, the pressure piston being designed such that a predetermined test pressure can be applied to the test volume, with an oil absorption or oil separation element coupled to the test volume so as to absorb oil or separate oil, and with a measuring means by which a quantity representative of a change of the test volume can be measured.

In central lubrication systems, lubricating grease is conducted from a central reservoir via a conduction system to a plurality of lubrication points. The central lubrication systems comprise lubricating grease dispatchers, for example metering valves, which distribute a predetermined amount of lubricating grease to the various lubrication points. Lubricating greases essentially consist of a solid phase, the thickener, and a liquid phase, the oil. Both phases are more or less well and durably mixed or combined with each other during the manufacturing process for the lubricating grease.

In central lubrication systems, failures can occur if a so-called bleeding of the lubricating grease by the residual pressure in the system occurs between individual lubrication intervals. During bleeding, the oil and the thickener are more or less separated. As the oil can escape due to its consistency, for example through a sealing clearance, the thickener is left and in the worst case causes a failure of the central lubrication system, e.g. by blocking a lubricating grease dispatcher. This results in stop periods of the machine or system to be lubricated with the corresponding consequences, such as loss of production, unplanned maintenance works, etc. In some cases, lubricating grease dispatchers have to be exchanged at possibly hardly accessible points.

To avoid the failure of a central lubrication system due to an oil separation of the lubricating grease, lubricating greases are tested for their oil separation tendencies before they are employed in a central lubrication system.

In the DE 94 16 284 U1, a test device is described with which lubricating greases can be tested for their oil separation tendencies. With the test device described in DE 94 16 284 U1, it can be detected whether a lubricating grease is suited for being employed in central lubrication systems or not.

Indeed, the test method with the device of DE 94 16 284 U1 provides a statement indicating whether a lubricating grease exceeds a limiting value of the oil separation tendency predetermined for the employment in a central lubrication system and is thus generally suited for being employed in the central lubrication system or not. However, not all central lubrication systems are comparable, and the method according to DE 94 16 281 U1 does not provide any specific statement indicating whether a lubricating grease is, for example, nevertheless suited for a central lubrication system with particularly short lubrication intervals. To be able to deliver a number of lubricating greases as high as possible despite their separation tendencies, there is a demand to find out when lubricating greases with higher oil separation tendencies can be employed in central lubrication systems.

Consequently, the object of the invention is to provide a test method and a test device for carrying out the test method with which the oil separation tendency of a lubricating grease can be detected more precisely than before.

This object is achieved for the test method according to the invention in that the time history of the change of the test volume representative of the oil separation is detected over the test period.

For the test device according to the invention, the object is achieved by a monitoring means connected to the measuring means so as to transmit signals by which a time history of the change of the test volume can be detected.

The advantage of the solution according to the invention is that by means of the time history of the change of the test volume representative of the oil separation, a maximally admissible dwell time of the lubricating grease in a central lubrication means can be determined. One can derive a presetting for the control times, such as delivery time and rest time, of a central lubrication system from this maximally admissible dwell time. In this manner, even lubricants with increased oil separation tendencies can be employed if a maximally admissible dwell time in the lubrication system is not exceeded.

The test method according to the invention as well as the test device according to the invention can be further developed by various independent embodiments which are each for themselves advantageous. Below, these embodiments and the respective advantages associated to the embodiments will be briefly discussed.

In the test method according to the invention, the volume change of the test volume can be detected by measuring a quantity representative of the test volume. The advantage is that the test method according to the invention can be carried out more easily with the same accuracy, as direct volume measurement is hardly possible. As a representative quantity, for example the relative motion of the pressure piston of the test device can be monitored as the pressure piston follows the volume change of the test volume.

To obtain a parameter usable for controlling a central lubrication system, a limit moment where the oil separation exceeds a predetermined limiting value can be determined from the time history. Furthermore, the time history of the change of the test volume as well as the limit moment can be stored to permit a later access.

To detect the oil separation tendency of a fat in dependency of the pressure and/or temperature, the test pressure and/or the temperature of the lubricating grease in the test volume can be maintained essentially constant within the test period.

For a test method for the determination of the oil separation tendency of a lubricating grease for different temperatures and/or test pressures, the above-mentioned method with its various embodiments can be repeated with changed temperature and/or changed test pressure. A group of curves for the oil separation tendency of a lubricating grease over the time and different limit moments can be detected, wherein each curve and each limit moment represents a certain temperature and a certain test pressure. With these specific limit moments, a central lubrication system can be controlled.

In an advantageous embodiment of the test device according to the invention, the monitoring means can be designed such that it detects a limit moment at which the oil separation exceeds a predetermined limiting value. The advantage is that the limit moment can be utilized as a control parameter of a central lubrication system.

Furthermore, the test device can comprise a temperature-control means for adjusting a predetermined temperature of the test volume. The advantage is that the testing of the lubricating grease sample can be carried out with various, predeterminable temperatures, and thus a statement on the temperature dependency of the oil separation tendency can be made. The temperature-control means can either control only the temperature of the test volume with the lubricating grease sample or, for example, the complete space where the test device is arranged.

Furthermore, the monitoring means can comprise a storage means and/or a display means by which the time history of the change of the test volume and the limit moment can be stored and/or displayed.

To generate the required test pressure during a test, the test device can comprise a force element by which an essentially constant force can be applied to the pressure piston. Such a force element can be, for example, a pneumatic cylinder, a weight or a spring.

In an advantageous further development, the monitoring means can generate a measurement curve from the measured values of the measuring means, i.e. the positions of the pressure piston. The advantage is that at any moment a certain quantity of oil separation can be read out from the measurement curve, even if the measuring means delivers a measured value e.g. only every five minutes. The measurement curve can be generated e.g. by interpolation and it can, for example, be smoothed. Thus, the limit moment can be determined more exactly. Furthermore, the monitoring means can generate a group of curves from several measurement curves which have been detected each at different test temperatures and/or test pressures for a lubricating grease. From such a group of curves of a lubricating grease, control parameters for a central lubrication system can be determined, such as e.g. the frequency of lubrication intervals in dependency of a residual pressure level, a dwell time of the lubricating grease and a lubricating grease temperature.

Apart from the above-described test method and test device, the invention also relates to a method for controlling a central lubrication system, where at lubrication intervals, a certain amount of lubricant is delivered to several lubrication points through lubricant lines. To be able to employ lubricating greases with an oil separation tendency without the central lubrication system failing due to oil separation, the invention provides a control of the distance of time between the lubrication intervals in dependency of a limiting point of time resp. time threshold.

To be able to exclude an oil separation of the lubricating grease in the central lubrication system even more reliably, the distance of time of the lubrication intervals can be controlled in dependency of the lubricating grease temperature and/or the pressure in the central lubrication system.

Below, the invention will be illustrated by way of example with reference to the accompanying drawings. The various features can be combined independently, as has already been explained above for the individual advantageous embodiments.

In the drawings:

FIG. 2 shows the test device according to the invention of FIG. 1 in a second position;

FIG. 3 shows the test device of FIGS. 1 and 2 in a third position;

Figure 1:
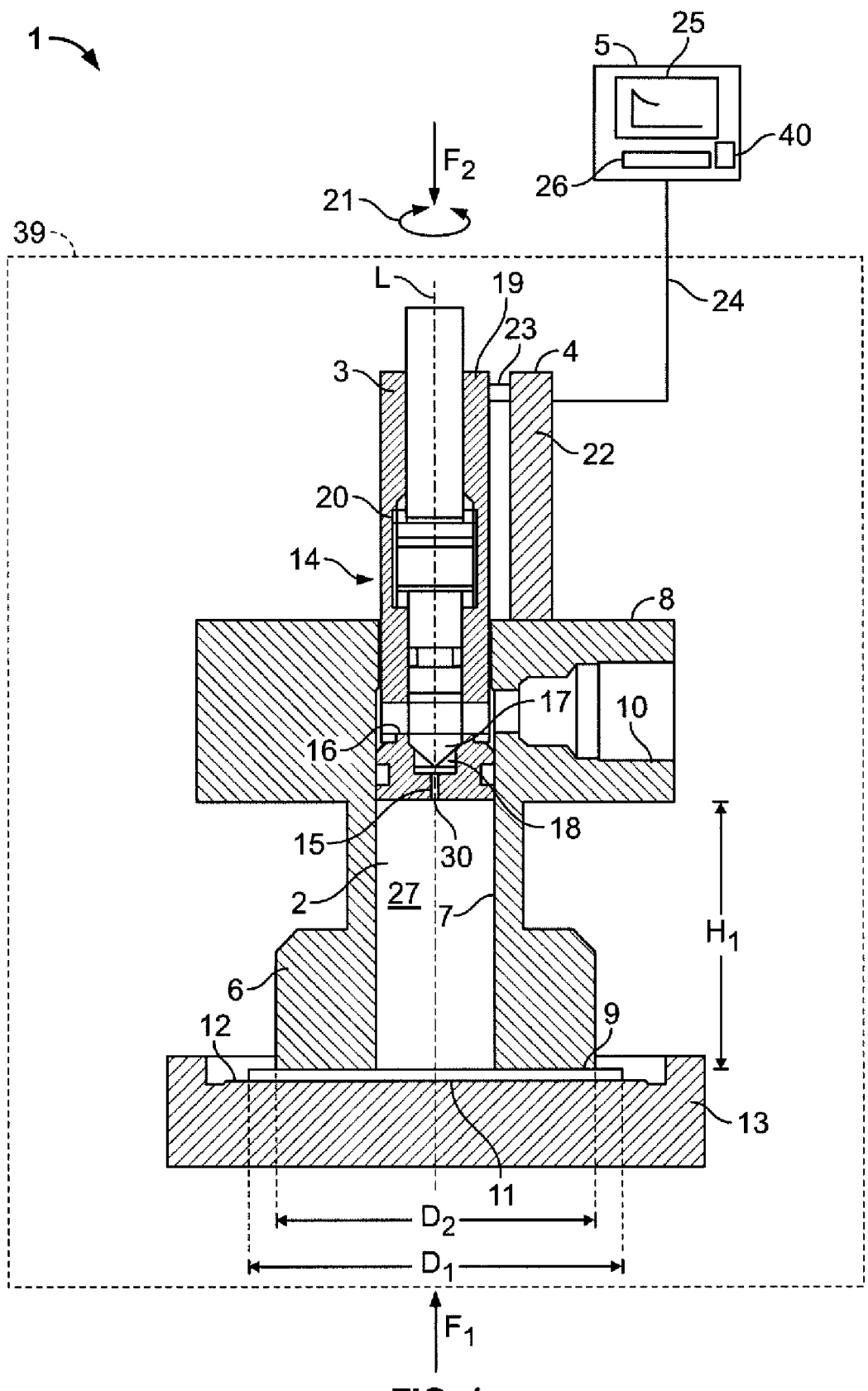
FIG. 1 shows a schematic representation of a test device according to the invention in a first position.

First, the general construction of a test device 1 according to the invention is described with reference to FIG. 1 and the exemplary embodiment represented therein.

The test device 1 comprises a test volume 2, a pressure piston 3 defining the test volume 2, a measuring means 4 as well as a monitoring unit 5 connected to the measuring means 4 so as to transmit signals.

The cylindrical test volume 2 is formed in a test cylinder 6 with a cylinder bore 7. At the upper end, the test volume 2 representing a test chamber is limited resp. defined or bordered by the pressure piston 3 arranged in the cylinder bore 7. In the embodiment in FIG. 1, the test cylinder 6 is rotationally symmetrically formed about a longitudinal axis L and has plane front faces 8, 9 essentially extending transversely to the longitudinal axis L. A disposal bore 10 is formed in the test cylinder 6 transversely to the longitudinal direction L and ends in the cylinder bore 7. In the embodiment in FIG. 1, the disposal bore 10 tapers step by step from the outside circumference of the test cylinder 6 towards the cylinder bore 7.

The test volume 2 is defined by an oil absorption or oil separation element 11 at the end opposite of the pressure piston 3. The oil absorption or oil separation element 11 is received in a pocket 12 of a pressure disk 13. The disk-shaped oil absorption or oil separation element 11 has a larger outside diameter D1 than the outside diameter D2 of the lower front face 9 of the test cylinder 6, so that the oil absorption or oil separation element 11 laterally protrudes from the test cylinder 6. The oil absorption or oil separation element 11 is arranged in the longitudinal direction L between the test cylinder 6 and the pressure disk 13. In the embodiment in FIG. 1, the pressure disk 13 is pressed against the test cylinder 6 by a force $F_1$ acting into the longitudinal direction L, so that the oil absorption or oil separation element 11 is pinched between the pressure disk 13 and the test cylinder 6. The pressure disk 13 can be connected to the test cylinder 6 by means of fastening means (not shown), such as screws.

In the embodiment in FIG. 1, the oil absorption or oil separation element 11 is made as a round filter element from an absorbent material, such as for example a filter paper. Alternatively, the oil absorption or oil separation element 11 can be made of any absorbent material that can absorb the separated oil or conduct the same out of the test volume 2. As another alternative, the oil separation element 11 can also be formed as a gap through which the oil can escape and/or which retains the lubricating grease.

The pressure piston 3 limiting the test volume 2 at the top has an essentially circular cylindrical shape and comprises a piston area 30 adjacent to the test volume 2, a nozzle bore 15, a cross hole 16, and a valve unit 14. The nozzle bore 15 extending on the longitudinal axis L ends in a cross hole 16 extending transversely to the longitudinal direction L. The valve unit 14 is formed in this ending region between the cross hole 16 and the nozzle bore 15 and in the position in FIG. 1 it closes the connection between the nozzle bore 15 and the cross hole 16. The valve unit 14 comprises a valve lifter 17 and a valve seat 18. The valve lifter 17 is arranged in a valve bore 19 in the pressure piston extending in the longitudinal direction L and connected to the pressure piston 3 via a thread 20. By means of a revolution 21, the valve lifter 17 can be moved relatively to the pressure piston 3 along the longitudinal axis L to and from by means of the thread 20, i.e. into and out of the valve seat 18. Thus, by the valve unit 14, the connection between the nozzle bore 15 and the cross hole 16 can be opened or closed, respectively. The pressure piston 3 is oriented with respect to the test cylinder 6 such that the cross hole 16 in the first stroke position which is shown in FIG. 1 is aligned with the disposal bore 10. In the first stroke position, the essentially plane piston area 30 has a distance $H_1$ to the oil absorption or oil separation element 11.

The pressure piston 3 is arranged along the longitudinal direction L in the cylinder bore 7 so as to be linearly movable. The outside diameter of the pressure piston 3 is essentially formed so as to equal the inside diameter of the cylinder bore 7, so that essentially no lubricating grease can escape from the test volume 2 and the test pressure can be kept constant. The cylinder bore 7 serves as guide surface for the pressure piston 3.

The measuring means 4 of the test device 1 is arranged on the upper front face 8 of the test cylinder 6 in the embodiment in FIG. 1. The measuring means 4 comprises a static portion 22 and a portion 23 movable with respect to the static portion 22 along the longitudinal direction L. The static portion 22 is connected to the test cylinder 6 and the movable portion 23 is connected to the pressure piston 3, in each case so as to transmit motions. The measuring means 4 is formed as a length measuring means, e.g. a commercially available incremental or analogue stroke measurement system, and detects a relative motion of the pressure piston 3 to the test cylinder 6.

The measuring means 4 is connected to the monitoring unit 5 via a connection line 24 so as to transmit signals. The monitoring unit 5 comprises a control unit 40, a display means 25, and a storage means 26. The control unit 40 processes the signals of the measuring means 4 and is connected to the display means 25 and the storage means 26. The display means 25 graphically represents the measuring signal of the measuring means 4 and is, for example, a monitor. The storage means 26 stores the measuring signals of the measuring means 4 or the graphic representation for later access or later processing. The storage means 26 is, for example, a hard-disk storage. The monitoring unit 5 is, for example, a PC to which the measuring means 4 is connected via an interface converter. The measuring signals can be written in the PC e.g. into spreadsheet software and graphically represented by means of this software.

The test device 1 further comprises a temperature-control means 39 which keeps the temperature within the test volume 2 at a predetermined variable temperature. In FIG. 1, the temperature-control means 39 controls the temperature of the whole test device 1. Alternatively, only the temperature of the test volume 2 can be controlled.

During the operation of the test device 1, for carrying out the test method according to the invention, the test volume 2, as represented in FIG. 1, is filled with lubricating grease 27 to be tested. Here, the pressure piston 3 is moved to a start position represented in FIG. 1. The test volume 2 can be filled with the valve unit 14 being closed and in the piston position which is shown in FIG. 1 ($H_1$) via the test cylinder 6 open at the bottom and swiveled to the front for filling. After filling, the cylinder 6 is again swiveled to the position shown in FIG. 1 and sealed with the oil separation element 11 in the pressure disk 13.

Now, the test operation is started by exerting an essentially constant force $F_2$ onto the pressure piston 3, e.g. by a pneumatic cylinder, a weight or a spring. Thus, an essentially constant test pressure is applied to the test volume 2 with the lubricating grease 27. Over a predetermined test period, for example 24 hours, the test pressure in the test volume 2 is kept essentially constant. By the temperature-control means 39, the temperature of the lubricating grease sample 27 in the test volume 2 is also kept constant.

Lubricating greases essentially consist of a solid phase, the thickener, and a liquid phase, the oil. Both phases are more or less well and durably mixed or combined with each other during the manufacturing process for the lubricant. Under the influence of pressure, the two phases can be more or less separated. This separation is referred to as oil separation. The oil separation of the lubricating grease sample 27 and a moment T at which the oil separation exceeds a predetermined limiting value $H_G$ are detected over the test period by the test method according to the invention with the test device 1. An oil separation above the limiting value $H_G$ can be critical for the operation of a central lubrication system.

FIG. 2 shows the test device 1 according to the invention at the end of the test period. With respect to FIG. 1, in the test volume 2 in FIG. 2, layers of still soft lubricating grease 27 and already hardened lubricating grease 28 have formed. Furthermore, in the pocket 12, separated oil 29 has collected around the oil absorption or oil separation element 11. The pressure piston 3 is in a stroke position in FIG. 2 in which the piston area 30 has a distance $H_2$ to the oil absorption or oil separation element 11. The distance $H_2$ at the end of the test period is smaller than the distance $H_1$ that the piston area 30 had at the beginning of the test period in FIG. 1.

Within the test period, the measuring means 4 has continuously detected the position of the pressure piston 3 and transmitted it to the monitoring unit 5 as measuring signal. The monitoring unit 5 has processed the measuring signals of the measuring means 4 to form a measurement curve.

FIG. 3 shows the test device 1 according to the invention, also after the termination of the test period, however in a position in which the soft or free-flowing lubricating grease 27 still present in FIG. 2 has been removed from the test volume 2. To this end, in the position in FIG. 2, the seat valve 14 has been opened, so that the nozzle bore 15 is connected to the disposal bore 10 as the pressure piston 3 is tapered at the outside diameter above the cross hole 16. As the force $F_2$ still acts on the pressure piston 3 and thus pressure is still applied to the lubricating grease 27 in the test volume 2, the lubricating grease 27 escapes from the disposal bore 10 and the pressure piston 3 moves to the position represented in FIG. 3 in which only hardened, no longer free-flowing lubricating grease is present in the test volume 2. In FIG. 3, the piston area 30 has a distance $H_3$ to the oil absorption or oil separation element 11. The distance $H_3$ is smaller than the distances $H_2$ and $H_1$. In the position of the test device 1 which is shown in FIG. 3, only hardened, no longer free-flowing lubricating grease is present in the test volume 2 and the piston area 30 rests on hardened plugs of lubricating grease 28. Thus, the height $H_3$ corresponds to the height of the hardened plugs of lubricating grease 28 in the test volume 2. Subsequently, the hardening height $H_3$ and the height $H_2$ representing the oil separation are put into relation to the height $H_1$ representing the overall volume. Thus, the probable thickener proportion of the lubricating grease is calculated.

Figure 4:
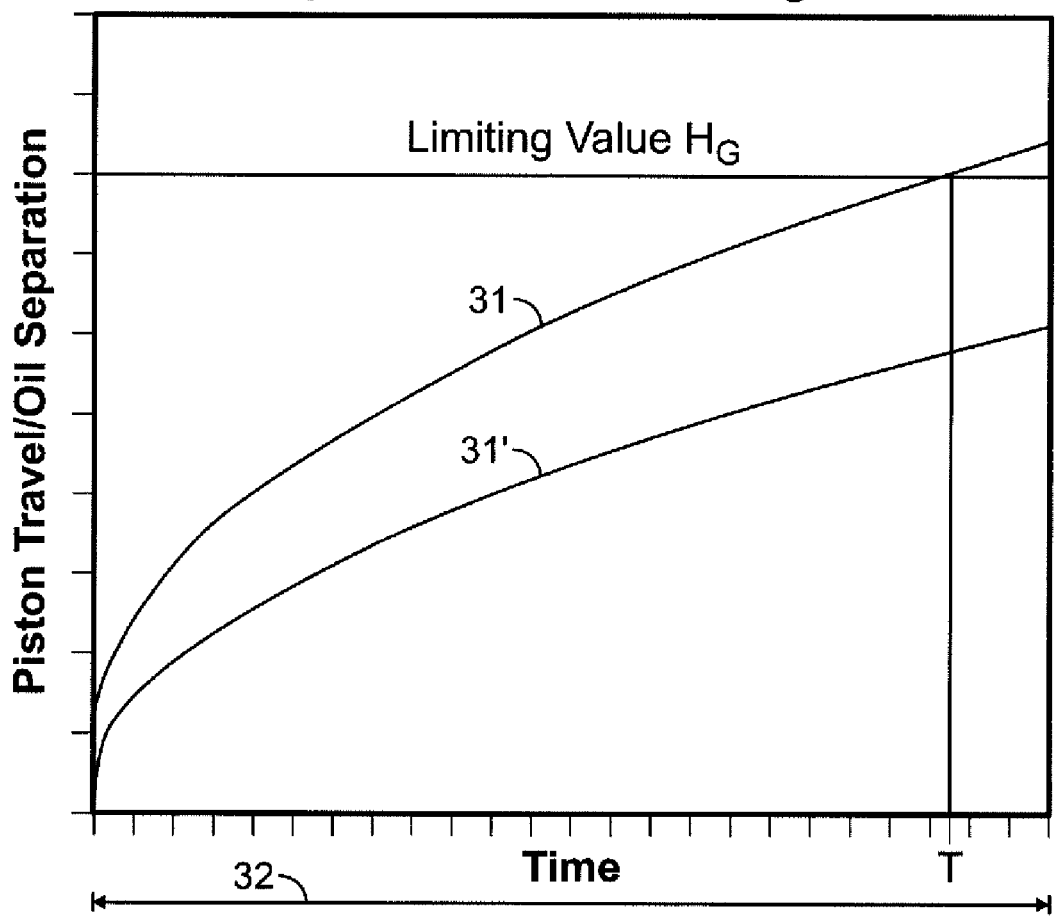
FIG. 4 shows a diagram of the oil separation of a lubricating grease, detected with the test device of FIGS. 1 to 3.

FIG. 4 shows two measurement curves 31, 31' that have been recorded by the monitoring unit 5 during two test operations. The measurement curves 31, 31' are shown in the diagram in FIG. 4 in a system of coordinates with the piston travel or the oil separation as ordinate and the time as abscissa. The measurement curve 31 shows the travel of the piston within the test period 32. The measurement curves 31, 31' shown in FIG. 4 each show the oil separation increasing over time as a function of the time history of the piston travel of two different lubricants. Additionally, for example other tests with different temperatures and/or test pressures can be carried out for the same lubricants.

In FIG. 4, a limiting value $H_G$ is plotted which represents an empirically determined, barely admissible oil separation. The measurement curve 31' of a lubricant A is always below the limiting value $H_G$ in the represented period. This lubricant can thus be classified as uncritical with respect to oil separation and would also have been classified as admissible by the known test methods for the determination of the oil separation tendency. The measurement curve 31 of another lubricant B exceeds the limiting value $H_G$ at a moment T. The determination of the time history of the oil separation and the moment T with the test method according to the invention shows that the lubricant B can be delivered in a central lubrication system until the moment T is achieved without the limiting value $H_G$ being exceeded. According to the known test methods, the lubricant B would have been classified as not being employable for a central lubrication system as it exceeds the limiting value $H_G$ at the end of the test period 32.

Figure 5:
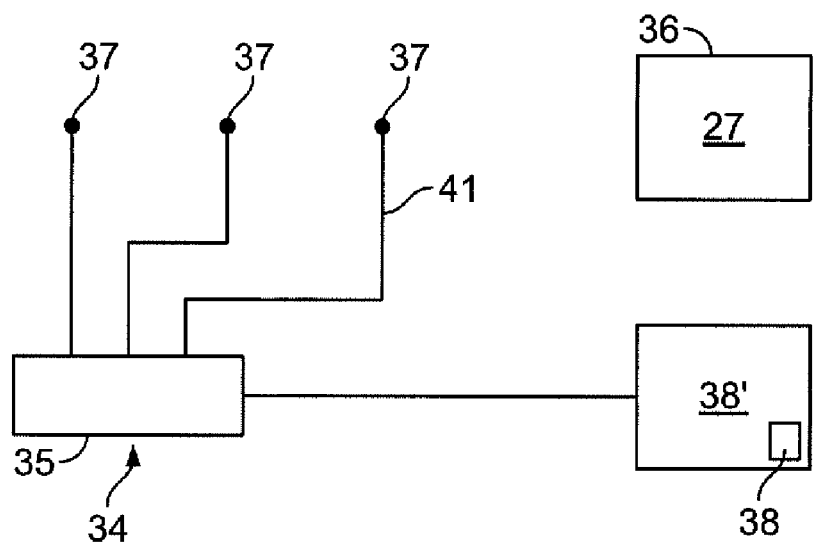
FIG. 5 shows a schematic representation of a central lubrication system according to the invention.

FIG. 5 shows a schematic representation of a central lubrication system 34 according to the invention with a metering valve 35 that with the aid of a lubricant pump 38' conducts lubricating grease 27 from a reservoir 36 to several lubrication points 37 via lubricant lines 41. The central lubrication system 34 further comprises a control unit 38 that can be e.g. integrated in the pump 38' which provides the metering valve 35 with lubricating grease. The lubricating grease 27 in FIG. 5 is the above described lubricant B with the measurement curve 31 of FIG. 4. To prevent the lubricating grease 27 from excessively bleeding within the central lubrication system 34 i.e. from separating oil, the distances of time between the individual lubrication intervals are controlled by means of parameters that can be read out from the diagram in FIG. 4. The time between the lubrication intervals is e.g. selected such that they are below the moment T as of which the oil separation of the lubricating grease exceeds the limiting value $H_G$. The moment T has been determined from the diagram in FIG. 4 and entered into the control unit 38 as a control parameter. The control unit 38 detects the temperature and the pressure within the central lubrication system 34, so that for different temperatures and pressures for which respective measurement curves can be determined, an associated critical moment T each can be entered and used.

The invention claimed is:

1. Test method for the determination of an oil separation tendency of lubricating greases under pressure load, wherein:
    a predetermined test pressure is applied to a test volume filled with lubricating grease during a predetermined test period,
    the lubricating grease of the test volume is contacted with an oil absorption or oil separation element, and
    a time history of the change of the test volume representative of an absorption or separation of oil separated from the lubricating grease by the oil absorption or oil separation element is detected over the test period.

2. Method according to claim 1, characterized in that a limiting point of time at which the oil separation exceeds a predetermined limiting value is determined from the time history.

3. Method according to claim 1, characterized in that the time history of the change of the test volume is stored after processing a signal of a measuring means.

4. Method according to claim 1, characterized in that the change of the test volume is detected by measuring a quantity representative of the test volume.

5. Method according to claim 1, characterized in that the test pressure and/or the temperature of the lubricating grease are kept essentially constant within the test period.

6. Test device for the determination of an oil separation tendency of lubricating greases under pressure load with a test volume for receiving a lubricating grease sample,
    with a pressure piston limiting the test volume by which the test volume is constituted such that a predetermined test pressure can be applied to the same,
    with an oil absorption or oil separation element coupled to the test volume so as to absorb oil or separate oil, and
    with a measuring means by which a quantity representative of a change of the test volume can be measured,
    characterized by a monitoring unit connected to the measuring means so as to transmit signals by which a time history of the change of the test volume can be detected.

7. Test device according to claim 6, characterized in that the monitoring unit is designed such that it detects a limiting point of time at which the oil separation exceeds a predetermined limiting value.

8. Test device according to claim 6 or 7, characterized in that the monitoring means comprises a storage means by which the time history of the change of the test volume and/or the limiting point of time can be stored.

9. Test device according to claim 6, characterized in that the monitoring means comprises a display means by which the time history of the change of the test volume and the limiting point of time can be displayed.

10. Test device according to claim 6, characterized in that the test device comprises a temperature-control means for adjusting a predetermined temperature of the test volume, the predetermined temperature being held constant over a test period by the temperature-control means.

11. Test device according to claim 10, characterized in that the temperature can be variably adjusted.

12. Method for controlling a central lubrication system in which
    at lubrication intervals, a predetermined amount of lubricating grease is delivered to several lubrication points through lubricant lines,
    characterized in that a length of time between the lubrication intervals is controlled in dependency of a limiting point of time at which a time history of an oil separation of the lubricating grease exceeds a predetermined limiting value.

13. Method according to claim 12, characterized in that the length of time between the lubrication intervals is controlled in dependency of a temperature and/or a pressure in the central lubrication system.

14. Method according to claim 2, characterized in that the time history of a change of the limiting point of time is stored.

15. Test method for providing an indication whether a lubricating grease is suitable for being employed in a central lubrication system or not, wherein
    a predetermined test pressure is applied to a test volume filled with lubricating grease,
    the lubricating grease of the test volume is contacted with an oil absorption or oil separation element, and
    a change of the test volume is detected on the basis of an absorption or separation of oil separated from the lubricating grease by the oil absorption or oil separation element,
    wherein a maximally admissible dwell time is determined by means of a time history of the change of the test volume representative of oil absorption or oil separation.

16. Test method for the determination of a temperature- and/or pressure-dependent oil separation tendency of a lubricating grease, in which the method according to one of claims 1 to 5 and 15 is repeated, in each of the repeated test periods with changed temperature or changed test pressure relative to another test period.

* * * * *